(12) United States Patent (10) Patent No.: US 8,970,830 B2
Margraf et al. (45) Date of Patent: Mar. 3, 2015

(54) MEASURING METHOD AND DEVICE FOR DETERMINING TRANSMISSION AND/OR REFLECTION PROPERTIES

(75) Inventors: Joerg Margraf, Jena (DE); Peter Lamparter, Jena (DE)

(73) Assignee: Carl Zeiss Microscopy GmbH, Jena (DE)

(*) Notice: Subject to any disclaimer, the term of this patent is extended or adjusted under 35 U.S.C. 154(b) by 363 days.

(21) Appl. No.: 13/492,306

(22) Filed: Jun. 8, 2012

(65) Prior Publication Data

US 2012/0314208 A1 Dec. 13, 2012

(30) Foreign Application Priority Data

Jun. 9, 2011 (DE) .......................... 10 2011 077 290

(51) Int. Cl.
*G01N 21/00* (2006.01)
*G01N 21/89* (2006.01)
(Continued)

(52) U.S. Cl.
CPC .......... *G01N 21/8901* (2013.01); *G01N 21/474* (2013.01); *G01N 21/896* (2013.01); *G01N 2201/065* (2013.01)
USPC ....................................................... 356/73

(58) Field of Classification Search
CPC ......... G01J 3/02; G01J 15/1459; G01J 21/65; G01J 3/513; G01J 3/51
USPC ....................................................... 356/73
See application file for complete search history.

(56) References Cited

U.S. PATENT DOCUMENTS 3,746,869 A 7/1973 Lindstedt et al.
4,120,582 A 10/1978 De Vries et al.
(Continued)

FOREIGN PATENT DOCUMENTS

DE 2 047 952 4/1972
DE 27 57 196 6/1979
(Continued)

OTHER PUBLICATIONS

Adrian H. Bachmann et al., "Resonant Doppler flow imaging and optical vivisection of retinal blood vessels", Jan. 22, 2007/vol. 15, No. 2/*Optics Express*, pp. 408-422.
(Continued)

*Primary Examiner* — Tarifur Chowdhury
*Assistant Examiner* — Md Rahman
(74) *Attorney, Agent, or Firm* — Patterson Thuente Pedersen, P.A.

(57) ABSTRACT

The disclosure relates to optical measuring methods and apparatus for determining the transmission and/or reflection properties of translucent objects with utility for process monitoring and quality inspection in the manufacture of surface-coated substrates. According to the disclosure the transmission and reflection properties are determined in such a way that sequentially:

a first large surface of the object is illuminated by a first illuminating device, with a photodetector measuring the total transmittance ($T_{total}$), a second, large surface of the object, lying opposite and parallel to the first one, is illuminated by a second illuminating device, with a photodetector measuring the diffuse transmittance ($T_{diffuse}$), and optionally the first large surface of the object is illuminated by the first illuminating device, with the photodetector measuring the reflectance, and/or the second large surface of the object is illuminated by the second illuminating device, with the photodetector measuring the reflectance.

8 Claims, 1 Drawing Sheet

(51) Int. Cl.
*G01N 21/47* (2006.01)
*G01N 21/896* (2006.01)

(56) References Cited

U.S. PATENT DOCUMENTS

| | | | |
|---|---|---|---|
| 4,602,160 A * | 7/1986 | Mactaggart | 250/341.5 |
| 8,259,294 B2 | 9/2012 | Proehl et al. | |
| 2002/0001078 A1 | 1/2002 | Gobel et al. | |
| 2003/0202180 A1 | 10/2003 | Gobel et al. | |
| 2010/0188651 A1 | 7/2010 | Kostuch et al. | |

FOREIGN PATENT DOCUMENTS

| | | |
|---|---|---|
| DE | 100 10 213 A1 | 9/2001 |
| DE | 102009040642 B3 | 3/2011 |
| DE | 102010001189 A1 | 7/2011 |

OTHER PUBLICATIONS

S.H. Yun et al., "Pulsed-source and swept-source spectral-domain optical coherence tomography with reduced motion artifacts", Nov. 15, 2004/vol. 12, No. 23/*Optics Express*, pp. 5614-5624.

Lin An et al., "Use of a scanner to modulate spatial interferograms for in vivo full-range Fourier-domain optical coherence tomography", Dec. 1, 2007/vol. 32, No. 23/*Optics Letters*, pp. 3423-3425.

* cited by examiner

MEASURING METHOD AND DEVICE FOR DETERMINING TRANSMISSION AND/OR REFLECTION PROPERTIES

CROSS REFERENCE TO RELATED APPLICATIONS

The present application claims priority to and full benefit of German National Patent Application No. DE 10 2011 077 290.1 filed 9 Jun. 2011 the entire contents of which are incorporated herein by reference.

FIELD OF THE DISCLOSURE

The present disclosure relates to optical measuring methods and apparatus for determining the transmission and/or reflection properties of translucent objects; in particular, with utility for process monitoring and quality inspection in the manufacture of surface-coated substrates and objects, especially large-surface objects. disclosure

BACKGROUND OF THE DISCLOSURE

In the manufacture of coated translucent materials, such as substrates provided, e.g., with electrically conductive coatings as used in photovoltaics, the inspection of the transparent and reflective properties of the substrate is important mainly with regard to achieving an optimum efficiency in the conversion of solar radiation to electricity.

An important parameter in this is haze, a wide-angle scattering of light. According to the American Society for Testing and Materials international ASTM D standard 1003 the detailed specification of which is hereby incorporated by reference herein, haze is defined as the percentage of the light passing a translucent object that is deflected in the object by more than 2.5° from its propagation direction and thus, when passing the object, is scattered out of a directed bundle of rays due to, e.g., surface roughness of the object.

Pursuant to ASTM D 1003, the haze of translucent objects (transmission haze) can be determined by placing the object in front of the light entrance port of an integrating sphere and illuminating it from the object side opposite the integrating sphere in such a way that the illuminating light transilluminates the object and enters the integrating sphere. The integrating sphere features a built-in photodetector, which receives the transmitted light and converts it into a measurement signal. The detection direction of this photosensor and the normal to the object surface (which normal constitutes a measuring axis) include a specified angle.

In a different measuring method also specified in ASTM D 1003, the integrating sphere itself is used as an illumination device. By means of the integrating sphere, the object placed in front of the sphere's light exit port is illuminated with diffuse light. In this case, the photodetector is arranged on the other side of the object, i.e., the side opposite the integrating sphere.

Within the integrating sphere in the latter case, a light trap is provided which can be activated and which, in the active state, blocks out the directional portion of the light so that it does not reach the photodetector. By alternately activating and deactivating the light trap, one can determine two different transmission parameters. One of them delivers a measure of diffuse transmittance ($T_{diffuse}$), i.e., the light scattered at an angle of $>2.5°$ due to the influence of the object, whereas the other parameter delivers a measure of total transmittance ($T_{total}$), with light scattered by the object at an angle of $\leq 2.5°$ only, if at all. From these two data, the haze of the object is determined by the formula Haze=$T_{diffuse}/T_{total} \cdot 100\%$.

German National Patent DE 100 10 213 B4 captioned, "Optical Reflection and Transmission Measurement Device for Quality Monitoring in a Continuous Process, has Signal Conditioning Unit Integrated in Measuring Head to Process Output Signals of Spectrometer,", which operates by the principle of spectroscopy is hereby incorporated herein. A pair of corresponding U.S. patent applications both captioned, "Optical Measuring Arrangement, in Particular for Quality Control in Continuous Processes" and published as US2003202180 (A1) and US2002001078 (A1) are also fully incorporated by reference herein. The measuring apparatus depicted and described in the foregoing patent records features a measuring head with an integrating sphere, which is used for the diffuse illumination of the measuring object. With this arrangement, the total transmittance ($T_{total}$) of the illuminating light through the object and the reflectance of the illuminating light from a surface of the object can be measured sequentially.

German National Patent DE 10 2009 040 642 B3 describes a method for measuring optical parameters of transparent, scattering measuring objects and an apparatus for applying this method, especially for the in-line measurement of various transmittance and reflectance data of plate-shaped or strip-like substrates that are given transparent coatings in a coating plant and it too is hereby incorporated by reference herein.

With the latter method, too, the measuring object is illuminated with diffuse light by means of an integrating sphere. The light passing the measuring object is simultaneously captured by means of two photodetectors having differing detection directions; in one of the two detection directions the radiation directed immediately at the photodetector is suppressed by means of a light trap. By this method and the apparatus for its execution it is possible to simultaneously determine the diffuse transmittance ($T_{diffuse}$) and the total transmittance ($T_{total}$). Provided in addition are two more photodetectors, of which one detects the diffuse luminous reflectance, and the other, the total luminous reflectance from one of the surfaces.

In connection with process monitoring and quality inspection in the manufacture of large-surface coated substrates, it is frequently required to determine both diffuse transmittance ($T_{diffuse}$) and total transmittance ($T_{total}$) as well as luminous reflectance from both surfaces of the substrate, i.e., reflectance from the coated as well as from the uncoated substrate surface, and that with low technical expenditure. With the methods and apparatuses available in prior art, this requirement cannot be met.

Therefore, the disclosure is based on the problem of finding a method and at least one apparatus that do not suffer from the drawbacks of prior art as described above.

SUMMARY OF THE INVENTION

According to the disclosure, measurements of the transmission and reflection properties of large-surface translucent objects, especially for inline-process monitoring and quality inspection in the manufacture of large-surface coated substrates are carried out by means of the process steps as specified herein.

Accordingly, in a first version of the present methods, measurement is made with only two illuminating devices emitting diffuse light and two photodetectors, in such a way that:

a first large surface of the object is illuminated with a first one of the illuminating devices, with simultaneous measurements being made of total transmittance ($T_{total}$) with a first photodetector opposite the object, and of reflectance from this large surface with a second photodetector provided on the side of this large surface, and subsequently, the second large surface of the object opposite the first one is illuminated with the second illuminating device, with simultaneous measurements being made of diffuse transmittance ($T_{diffuse}$) with the second photodetector, and reflectance from this large surface with the first photodetector.

In an alternative version of the invented method, measurement is also made with only two illuminating devices emitting diffuse light and two photodetectors, in such a way that:

a first large surface of the object is illuminated with a first one of the illuminating devices, with total transmittance ($T_{total}$) being measured with a first photodetector, and the second large surface of the object opposite the first one is illuminated with the second illuminating device, with diffuse transmittance ($T_{diffuse}$) being measured with the second photodetector.

Supplementary, optional measurements can be made in such a way that:

the first large surface of the object is illuminated with the first illuminating device, with reflectance from this large surface being measured with the second photodetector, the second large surface of the object is illuminated with reflectance from this large surface being measured with the first photodetector.

In both versions, the succession of the two or four process steps, respectively, constitutes one measurement cycle, with which the transmission and reflection properties are determined for an area of a large-surface translucent object. The order of process steps within a measurement cycle can be varied at will or as required by the respective measurement job. It is within the scope of the disclosure to form measurement cycles that are concerned only with the determination of the two transmission data ($T_{diffuse}$ and $T_{total}$) or only with the determination of the reflection properties of the object surfaces lying opposite to each other.

The measurement data acquired during a measurement cycle are transmitted to a computer equipped with analysis software and connected to an information output device, which makes the data acquired (concerning diffuse transmittance ($T_{diffuse}$) and total transmittance ($T_{total}$) as well as the reflection properties of the two object surfaces) available for assessment or further processing, such as, e.g., for computing the haze value as the relationship of $T_{diffuse}/T_{total} \cdot 100\%$.

It is a substantial advantage of the present methods that it permits the transmission and reflection properties to be determined with less complex equipment configuration than in prior art; this advantage applies to both versions of the methods herein.

The two illuminating devices and the two photosensors are arranged in fixed positions relative to one another. Relative to the object, one of the illuminating devices and one of the photodetectors is spatially assigned to a first large surface of the object, whereas the other illuminating source and the second photodetector are spatially assigned to the opposite large surface, in such a way that one illuminating device and one photodetector are arranged on one side of the object and, facing them, the other illuminating source and the second photodetector on the other side of the object. Preferably, the illuminating devices lie on a common axis (for the purposes of the disclosure termed the measuring axis), which is a normal to the large surfaces of the object.

The illuminating devices are switched on alternately, so that only one of the two large surfaces is transilluminated for transmittance measurement or illuminated for reflectance measurement at a time.

The photodetectors used are of the direction-sensitive type. For achieving or amplifying their direction sensitivity, direction-sensitive optics may be arranged in front of the photodetectors.

The detection directions of the two photodetectors are oriented with an inclination relative to each other and to the measuring axis. In a preferred embodiment of the method, the two detection directions and the measuring axis are inclined relative to one another in such a way as to intersect. Favorably, the intersection point can be positioned into the object, viz. between the two large surfaces of the object.

The detection direction of one of the photodetectors is oriented in such a way that, for reflection measurement, it always points to a large surface of the object and, for measurement of diffuse transmittance ($T_{diffuse}$), to a light trap positioned opposite the object, which light trap blocks out the direct share of the illuminating light which is incident on, and passing, the object from the illuminating device on the opposite side of the object.

The detection direction of another photodetector is oriented in such a way that, for reflection measurement, it always points to the other large surface of the object and, for measurement of total transmittance ($T_{total}$), to a surface opposite the object which reflects the illuminating light and does not block out the direct share of the illuminating light.

Further, the measuring axis and the detection direction of the first photodetector lie in a first measuring plane, whereas the measuring axis and the detection direction of the second to photodetector lie in a second measuring plane. According to the disclosure, these two measuring planes are positioned in such a way that the preferably include an angle of $\alpha \neq 180°$ or, with particular preference, of $\alpha = 90°$, in order to prevent, in reflection measurement, the detection direction of the first photodetector pointing to the light trap and thus measuring only the reflectance of the diffuse share of the illuminating light. Accordingly, the angle $\alpha = 180°$ is selected only for such measuring jobs in which the reflectance of the diffuse share is of interest.

The illuminating devices are preferable integrating spheres, each with a light source built in. The integrating spheres are positioned on either side of the object and centered with the measuring axis. The detection directions of the two photodetectors point to the opposite integrating sphere each.

Apart from general applications for objects of various kinds, the present methods are, to particular advantage, suitable for shop-floor quality inspection in the manufacture of surface-coated substrates. For this purpose, the substrate is moved past the two illuminating devices. In a succession of periodically repeated measurement cycles, the described optical parameters are acquired of substrate areas the spatial extension of which, as seen in the direction of movement, is determined by the sum of the illuminating periods in the various measuring phases, the sum of the time intervals between the measuring phases, and the speed at which the substrate is moved. To keep this spatial extension of the substrate area to be measured as small as possible, the illumination of the substrate within each measurement cycle is done preferably in a stroboscopic manner, so that an optimum ratio between the duration of the measurement and the speed of the substrate movement is achieved.

By the present methods, measurement of the transmission properties can be performed in accordance with the specifications of the international standard ASTM D 1003.

The disclosure further relates to an optical measuring apparatus for applying the present methods. This measuring apparatus basically comprises:

- a first illuminating device in the form of an integrating sphere, from which diffuse light is directed through a light exit port onto a first large surface of the object,
- a second illuminating device in the form of an integrating sphere, from which diffuse light is directed through a light exit port onto the second large surface of the object situated opposite and parallel to the first large surface of the object,
- a photodetector, the detection direction of which points through both light exit ports to a light trap provided on the inside wall of the second illuminating device, which light trap blocks off the direct share of the illuminating light,
- another photodetector, the detection direction of which points through both light exit ports to the light-reflecting inside wall of the first illuminating device.

Either integrating sphere is provided with a light source that can be switched on and off, with both light sources being connected to control circuits for switching them on alternately, wherein:

- for measuring diffuse transmittance ($T_{diffuse}$) and/or for measuring reflectance of the large surface, the light source in the first illuminating device is switched on,
- for measuring total transmittance ($T_{total}$) and/or for measuring reflectance of the large surface, the light source in the second illuminating device is switched on, and wherein:

- the photodetectors are connected to a data analysis circuit at least during the time the light sources are switched on.

In one form of the foregoing, the photodetectors are fitted in the inside wall of the integrating sphere assigned to each.

In another embodiment, the integrating spheres are provided with reference photodetectors, the detection directions of which are directed at the reflecting inner surface of the respective integrating sphere for the purpose of acquiring reference signals. Furthermore, screening means are provided within the integrating spheres, which prevent light emitted by the light source from directly hitting the photodetectors provided for the acquisition of measurement data as well as those for the acquisition of reference data.

Further, the detection directions of the two photodetectors and the normal to the large surfaces are preferably inclined relative to each other in such a way that they have a common intersection point, which is located within the object, i.e. between its two large surfaces, with the normal constituting a measuring axis relative to the two detection directions.

The detection directions of the two photodetectors can each include with the normal, i.e., the measuring axis, an angle of 8°, so that the specification of the ASTM D 1003 standard is met.

Especially with regard to acquiring the reflection data, detection directions of the first and the second photosensor lie in different measuring planes, e.g., in measuring planes spaced from each other at an angle of 90° about the normal in order to prevent, in reflection measurement, the detection direction of the first photodetector from being directed at the light trap and thus measuring only the reflectance of the diffuse share of the illuminating light, as explained below in the context of an exemplary embodiment.

Especially for those embodiments of the disclosure in which a relative movement between the object and the measuring apparatus is provided, the light exit ports of the integrating spheres are arranged at such distances to the object that permit unobstructed relative movement.

DETAILED DESCRIPTION OF THE DISCLOSURE

Figure 1:
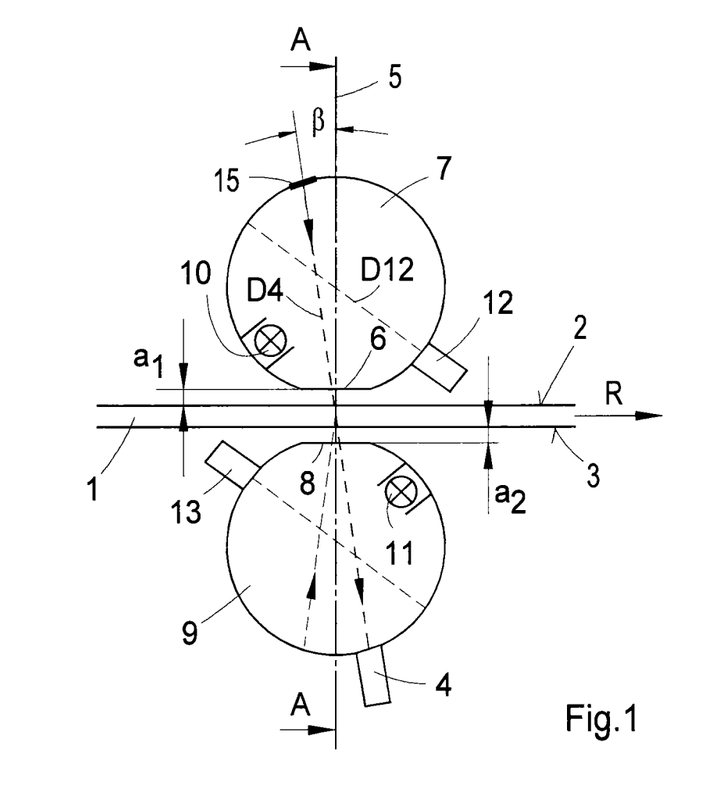
FIG. 1 illustrates the principle of the invented measuring apparatus by a section through a plane in which lie the measuring axis, the detection direction of one of two photodetectors and the direction of movement of a large-surface substrate coated on one side, of which the haze and the reflection properties of both the coated and the uncoated large surface are to be measured periodically.

FIG. 1 symbolically shows a strip-shaped, translucent object 1—here, for example, a substrate which is to be provided with a transparent, electrically conductive coating on its large surface 2 in an inline coating plant. In this process, the object 1 is continually moved in the direction R (indicated by an arrow in FIG. 1), in which, following the coating process, the object passes the present measuring apparatus as shown in FIG. 1.

In the example depicted in FIG. 1, let the quality inspection refer to the measurement and assessment of the transmission properties of the coated object and to the measurement of the reflectivities of both the coated large surface 2 and the uncoated large surface 3 of the object 1. The measurement is performed periodically while the substrate strip continuously moves past the measuring apparatus.

For determining the transmission properties, the measuring method to be applied is that specified in the international ASTM D 1003 standard; accordingly, what is to be measured is the total transmitted share $T_{total}$, which comprises both the directional and the diffuse transmittance ($T_{diffuse}$) of the illuminating light, and the diffusely transmitted share $T_{diffuse}$, which comprises only the diffuse share of the illuminating light. The transmission data $T_{diffuse}$ and $T_{total}$ thus determined can subsequently be processed to obtain a haze value by the function $T_{diffuse}/T_{total} \cdot 100\%$.

The reflection properties for the two large surfaces 2, 3 then are to be assessed according to the reflected illuminating light.

FIG. 1 shows the invented measuring apparatus in a section through a plane in which lie a photodetector 4, its detection direction D4, the measuring axis 5, which at the same time is a normal to the large surfaces 2, 3, and the moving direction R of the object 1. The detection direction D4 and the measuring axis 5 preferably include an angle β=8° therebetween which satisfies the specification of the international standard. Angles deviating from that measure are possible, of course, but will deliver deviating measurement results.

Arranged at a distance a1 from the large surface 2 is the light exit port 6 of an illuminating device 7, which is configured as an integrating sphere, emits diffuse light and is intended to illuminate the object 1 from the side of the coated large surface 2. Arranged opposite the object 1, at a distance a2 from the large surface 3, is the light exit port 8 of another illuminating device 9, which is also configured as an integrating sphere, emits diffuse light and is intended to illuminate the object 1 from the side of the coated large surface 3. The distances a1 and a2 are kept as small as possible. They are merely of a size permitting unobstructed movement of the object 1 relative to the two illuminating devices 7, 9.

A light source 10 is fitted in the illuminating device 7, and a light source 11 is provided in the illuminating device 9. Both light sources 10, 11 are configured, e.g., as high-power LEDs that can be switched on for short times; for the purpose of switching on, they are connected to a control circuit, which is not shown on the drawing. The illuminating device 7 is provided with a light trap 15, at which the detection direction D4 of the photodetector 4 is directed.

To enable the user to assess any distortions of the characteristics of the illuminating light exiting from the illuminating devices 7, 9 and hitting the large surface 2 or 3, respectively, and to make allowance for such distortions in the measurement results (such distortions being caused, for example, by the influence of scattered ambient light due to the distances a1, a2), the two illuminating devices 7, 9 are provided with photodetectors 12 and 13 the detection directions D12, D13 of which are directed at the reflecting inside wall of the illuminating device 7 or 9, respectively. The signal outlet ports of these reference photodetectors 12, 13, like the signal outlet ports of the photodetectors 4, 14, are connected to a data analysis circuit not shown on the drawing.

The photodetector 4 and the reference photodetectors 12, 13 are positioned in such a way that no direct light from the light sources 10, 11 can hit them. To avoid such direct light incidence and the ensuing distortion of the measurement results, screening means may be provided where necessary.

Figure 2:
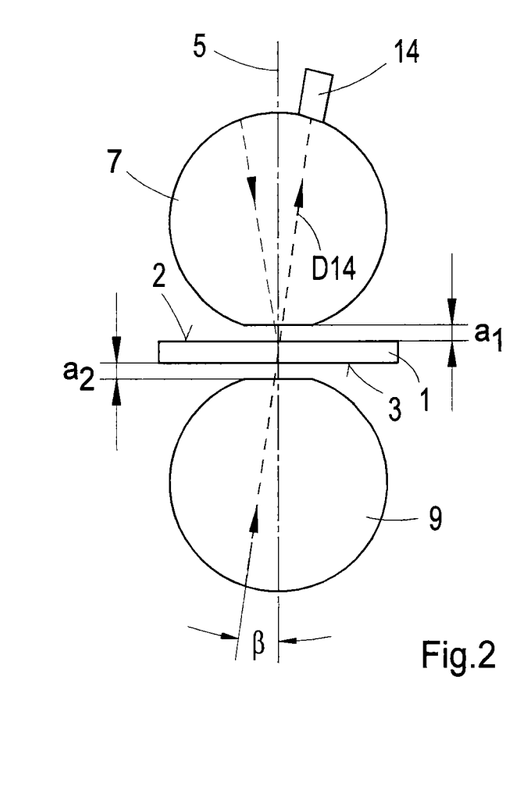
FIG. 2 illustrates the principle of the invented measuring apparatus according to FIG. 1, but by a section through a plane in which lie the measuring axis and the detection direction of the other photodetector, whereas the direction of movement of the substrate is normal to the plane of the drawing.

FIG. 2 shows a section A-A from FIG. 1. In FIG. 2 there can be seen again the object 1 (here sectioned across its strip width, though), the measuring axis 5, the illuminating devices 7 and 9 arranged symmetrically to the measuring axis 5, and the distances a1, a2 between the object 1 and the light exit ports 6 and 8, respectively. Here, the direction of movement of the object 1 is perpendicular to the plane of the drawing. For the sake of clarity, the photodetector 4 and the light source 11 actually belonging to the illuminating device 9, and the reference photodetector 12 actually belonging to the illuminating device 7 have been left out of the drawing.

In FIG. 2 there can be seen, however, fitted in the illuminating device 7 in this plane, a photodetector 14 and its detection direction D14, which points to the inner surface of the opposite illuminating device 9.

Looking at FIG. 1 and FIG. 2 together, one can see that the measuring axis 5 and the detection direction D4 lie in the plane shown in FIG. 1, whereas the measuring axis 5 and the detection direction D14 lie in the plane shown in FIG. 2. Both planes constitute measuring planes, which are offset from each other by an angle of 90° about the measuring axis 5. Here, the reference detection directions D12 and D13 lie in the plane of FIG. 1 for example only.

The invented measuring method in its first version is used with this apparatus as follows, with the order of the two process steps being selectable:

The large surface 3 of the object 1 is illuminated by the first illuminating device 9, with the photodetector 14 measuring the total transmittance ($T_{total}$) and the photodetector 4 simultaneously measuring the reflectance of the large surface 3;

The second large surface 2 of the object 1 (lying opposite the first one) is illuminated by the second illuminating device 7, with the second photodetector 4 measuring the diffuse transmittance ($T_{diffuse}$) and the photodetector 14 simultaneously measuring the reflectance of this large surface 2.

The second version of the invented measuring method can be employed with this apparatus as follows, with the order of the four process steps being selectable, and with the two last-named steps, concerning reflectance measurements, being optional:

The object 1 is transilluminated by a first illuminating device 9, with a first photodetector 14 measuring the total transmittance ($T_{total}$);

The object 1 is transilluminated by a second illuminating device 7, with the second photodetector 4 measuring the diffuse transmittance ($T_{diffuse}$);

The first large surface 3 of the object 1 is illuminated by the first illuminating device 9, with the second photodetector 4 measuring the reflectance of this large surface 3;

The second large surface 2 of the object 1 is illuminated by the second illuminating device 7, with the first photodetector 14 measuring the reflectance of this large surface 2.

As described above, the process steps in either version of the method form a measurement cycle. The measured data collected by the two photodetectors 4 and 14 during the measurement cycles are transmitted to a computer equipped with analysis software, in which the data determined for diffuse transmittance ($T_{diffuse}$) and total transmittance ($T_{total}$) as well as for the reflection properties of the two large surfaces 2, 3 are assessed and processed, such as, e.g., by combination into a haze value via the function $T_{diffuse}/T_{total} \cdot 100\%$.

We claim:

1. An optical measuring method usable for process monitoring and quality inspection in the manufacture of surface-coated substrates on a translucent object having a first large surface and a second large surface, utilizing a first illuminating device configured as a first integrating sphere having a first light exit port and a reflecting inside wall, a first direction sensitive photodetector, a second direction sensitive photodetector, a light trap and a second illuminating device configured as a second integrating sphere having a second light exit port and a reflecting inside wall, the method comprising one of a first procedure ("I") or a second procedure ("II"), the method comprising;

I. measuring transmission and reflection properties of the translucent object by:

illuminating the first large surface of the translucent object with the first illuminating device configured as the first integrating sphere that emits diffuse light through the first light exit port onto the first large surface of the translucent object, simultaneously measuring with the first direction sensitive photodetector a total transmittance ($T_{total}$) and with the second direction sensitive photodetector a first reflectance of the first large surface of the translucent object;

locating the light trap in a detection direction of the first direction sensitive photodetector;

illuminating the second large surface of the translucent object, lying opposite the first large surface with the second illuminating device configured as the second integrating sphere that emits diffuse light through the second light exit port onto the second large surface of the translucent object lying opposite the first large surface; and simultaneously measuring with the second direction sensitive photodetector, a detection direction of which is aligned with the first and the second light exit ports and to the reflecting inside wall of the first illuminating device a diffuse transmittance ($T_{diffuse}$) and with the first direction sensitive photodetector a second reflectance of the second large surface wherein respective detection directions of the first and the second direction-sensitive photodetectors are disposed in different measuring planes, or II, measuring transmission and reflection properties of the translucent object in any order, performing the following:

illuminating the first large surface of the translucent object with the first illuminating device configured as the first integrating sphere that emits diffuse light through the first light exit port onto the first large surface of the translucent object;

measuring with the first direction sensitive photodetector the total transmittance ($T_{total}$) of the first large surface;

illuminating the second large surface of the translucent object, lying opposite the first large surface with the second illuminating device configured as the second integrating sphere that emits diffuse light from which light is directed through the second light exit port;

locating the light trap in a detection direction of the first direction sensitive photodetector; and measuring with the second direction sensitive photodetector, the detection direction of which is aligned with the first and the second light exit ports and to the reflecting inside wall of the first illuminating device, the diffuse transmittance ($T_{diffuse}$) of the second large surface wherein the respective detection directions of the first and the second direction-sensitive photodetectors are disposed in different measuring planes.

2. An optical measuring method as claimed in claim 1, in which, in case of a sequential measurement, additionally, one of:

while the first large surface of the object is illuminated by the first illuminating device, measuring with the second photodetector the reflectance of this large surface, and while the second large surface of the object is illuminated by the second illuminating device, measuring with the first photodetector the reflectance of the second large surface.

3. An optical measuring method according to claim 1, wherein:

the first and the second illuminating devices and the first and the second photodetectors are arranged in fixed positions relative to each other, and relative to the object, the first illuminating device and the first photodetector are spatially assigned to the first large surface of the object and the second illuminating device and the second photodetector are spatially assigned to the second large surface, and the first and the second illuminating devices are switched on alternately so that only one of the first and the second large surfaces are illuminated at a given moment in time.

4. An optical measuring method according to claim 1, in which one of a pair of direction-sensitive photodetectors comprise the first and second photodetetors and an assembly of direction-sensitive optics are arranged in front of the first and the second photodetectors.

5. An optical measuring method according to claim 1, wherein each said integrating sphere has a light source built into the structure thereof.

6. An optical measuring method according to claim 1, further comprising:

moving in a direction "R" the first and second large surfaces perpendicularly to and between the first and second illuminating devices past a field of illumination of the first and second illuminating devices, wherein the spatial extension in moving the first and second large surfaces in the direction R defines an area covered during a measurement is determined by the following parameters:

the respective duration of illumination, the time-distances between the measurements, and the moving speed, and in which the measurements are repeated periodically to measure a great number of locations of the first and second large surfaces.

7. An optical measuring method according to claim 1, in which the measurement of the transmission properties is made according to the specifications of the international standard ASTM D 1003.

8. An optical measuring method according to claim 1, in which a haze characteristic of one of the first large surface and the second large surface is determined from the measurement results for total transmittance ($T_{total}$) and diffuse transmittance ($T_{diffuse}$) according to the function: Haze=$T_{diffuse}/T_{total}*100\%$.

* * * * *

UNITED STATES PATENT AND TRADEMARK OFFICE
CERTIFICATE OF CORRECTION

| | | |
|---|---|---|
| PATENT NO. | : 8,970,830 B2 | Page 1 of 3 |
| APPLICATION NO. | : 13/492306 | |
| DATED | : March 3, 2015 | |
| INVENTOR(S) | : Joerg Margraf et al. | |

It is certified that error appears in the above-identified patent and that said Letters Patent is hereby corrected as shown below:

The Title page, showing the illustrative figure, should be deleted and substitute therefor the attached Title page In the drawings Please replace FIG. 1 with FIG. 1 as shown on the attached pages In the specification

Col. 1, line 21, delete "disclosure"

Col. 2, line 7, delete the second occurrence of the ","

In the claims

Col. 10, line 14, delete "photodetetors" with --photodetectors--

Signed and Sealed this
Ninth Day of February, 2016

Michelle K. Lee
*Director of the United States Patent and Trademark Office*

(12) United States Patent
Margraf et al.

(10) Patent No.: US 8,970,830 B2
(45) Date of Patent: Mar. 3, 2015

(54) MEASURING METHOD AND DEVICE FOR DETERMINING TRANSMISSION AND/OR REFLECTION PROPERTIES

(75) Inventors: Joerg Margraf, Jena (DE); Peter Lamparter, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 363 days.

(21) Appl. No.: 13/492,306

(22) Filed: Jun. 8, 2012

(65) Prior Publication Data
US 2012/0314208 A1   Dec. 13, 2012

(30) Foreign Application Priority Data
Jun. 9, 2011 (DE) .................. 10 2011 077 290

(51) Int. Cl.
*G01N 21/00* (2006.01)
*G01N 21/89* (2006.01)
(Continued)

(52) U.S. Cl.
CPC ......... *G01N 21/8901* (2013.01); *G01N 21/474* (2013.01); *G01N 21/896* (2013.01); *G01N 2201/065* (2013.01)
USPC .................................. 356/73

(58) Field of Classification Search
CPC ......... G01J 3/02; G01J 15/1459; G01J 21/65; G01J 3/513; G01J 3/51
USPC .................................. 356/73
See application file for complete search history.

(56) References Cited

U.S. PATENT DOCUMENTS

| 3,746,869 A | 7/1973 | Lindstedt et al. |
| 4,120,582 A | 10/1978 | De Vries et al. |

(Continued)

FOREIGN PATENT DOCUMENTS

| DE | 2 047 952 | 4/1972 |
| DE | 27 57 196 | 6/1979 |

(Continued)

OTHER PUBLICATIONS

Adrian H. Bachmann et al., "Resonant Doppler flow imaging and optical vivisection of retinal blood vessels", Jan. 22, 2007/vol. 15, No. 2/*Optics Express*, pp. 408-422.

(Continued)

*Primary Examiner* — Tarifur Chowdhury
*Assistant Examiner* — Md Rahman
(74) *Attorney, Agent, or Firm* — Patterson Thuente Pedersen, P.A.

(57) ABSTRACT

The disclosure relates to optical measuring methods and apparatus for determining the transmission and/or reflection properties of translucent objects with utility for process monitoring and quality inspection in the manufacture of surface-coated substrates. According to the disclosure the transmission and reflection properties are determined in such a way that sequentially:

- a first large surface of the object is illuminated by a first illuminating device, with a photodetector measuring the total transmittance ($T_{total}$);
- a second, large surface of the object, lying opposite and parallel to the first one, is illuminated by a second illuminating device, with a photodetector measuring the diffuse transmittance ($T_{diffuse}$), and optionally
- the first large surface of the object is illuminated by the first illuminating device, with the photodetector measuring the reflectance, and/or
- the second large surface of the object is illuminated by the second illuminating device, with the photodetector measuring the reflectance.

8 Claims, 1 Drawing Sheet

Fig.2

Fig.1